United States Patent [19]

Graebner et al.

[11] Patent Number: 5,664,884

[45] Date of Patent: Sep. 9, 1997

[54] APPARATUS FOR DETERMINING THE THERMAL RESISTIVITY OF ELECTRICALLY INSULATING CRYSTALLINE MATERIALS

[75] Inventors: John Edwin Graebner, Short Hills; Sungho Jin, Millington, both of N.J.

[73] Assignee: Lucent Technologies Inc., Murray Hill, N.J.

[21] Appl. No.: 509,267

[22] Filed: Jul. 31, 1995

[51] Int. Cl.$^6$ .............................. G01N 25/20; G01N 25/18
[52] U.S. Cl. .............................. 374/43; 374/44; 364/556
[58] Field of Search ..................... 374/43, 44; 364/556

[56] References Cited

U.S. PATENT DOCUMENTS

| 3,552,185 | 1/1971 | Goode, Jr. et al. | 374/44 |
| 3,611,786 | 10/1971 | Schorr | 374/44 |
| 4,372,691 | 2/1983 | Buckley | 374/44 |
| 4,522,512 | 6/1985 | Atkins | 374/44 |
| 5,297,868 | 3/1994 | Graebner | 374/44 |
| 5,302,022 | 4/1994 | Huang et al. | 374/43 |

FOREIGN PATENT DOCUMENTS

| 2592490 | 7/1987 | France | 374/43 |
| 161649 | 12/1981 | Japan | 374/43 |

OTHER PUBLICATIONS

E. A. Burgemeister, "Thermal Conductivity of Natural Diamond Between 320 and 450 K," *Physica 93B* (1978) pp. 165–179.

D. T. Morelli et al., "Correlating Optical Absorption and Thermal Conductivity in Diamond," *Appl. Phys. Lett.* vol. 63, No. 2, Jul. 12, 1993, pp. 165–167.

*Elementary Physics: Classical and Modern*, by Richard T. Weidner and Robert L. Sells, pp. 306–307 (1975).

*Optics Guide 5*, published by Melles Griot, Irvine, CA 92714, at pp. 22–29 through 22–38 (1990).

Primary Examiner—Diego F. F. Gutierrez
Attorney, Agent, or Firm—David I. Caplan; Eugen E. Pacher

[57] ABSTRACT

This invention involves apparatus for determining the thermal resistivities $W_s$ ($=1/\kappa_s$) of electrically insulating, crystalline or polycrystalline samples under test (SUTs), all comprising host material such as CVD diamond. Once the optical absorptivities $\alpha_1$ and $\alpha_2$ and the thermal resistivities $W_1$ and $W_2$ of at least two other crystalline or polycrystalline bodies $B_1$ and $B_2$, respectively, comprising the same host material as the SUTs, and containing the same type of impurity or combination of impurities as the SUTs, are measured by some other technique—the inventive apparatus can then determine the thermal resistivities $W_s$ of the SUTs rather quickly from a measurement only of the optical absorptivities $a_s$ of the SUTs. These determinations of the thermal resistivities $W_s$ of the SUTs rely on our discovery that the following linear relationship exists: $W=A+C\alpha$, where A and C are constants so long as the type of impurity or combination of impurities in all the bodies $B_1$, $B_2$, and SUTs is the same, even though the impurities or combination of impurities have different concentrations in the bodies $B_1$ and $B_2$, as well as in the SUTs.

12 Claims, 2 Drawing Sheets

APPARATUS FOR DETERMINING THE THERMAL RESISTIVITY OF ELECTRICALLY INSULATING CRYSTALLINE MATERIALS

FIELD OF THE INVENTION

This invention relates to apparatus for determining the thermal resistivity of crystalline materials, and more particularly, of determining the thermal conductivity of electrically insulating materials such as the thermal conductivity of artificial and natural crystalline and polycrystalline materials like CVD diamond.

BACKGROUND OF THE INVENTION

In the case of one-dimensional steady-state heat flow through a sample body, its thermal conductivity $\kappa$ is given by $$\kappa = P/[A(\Delta T/\Delta x)] \tag{1}$$

where P is the heat flowing per unit time along the x axis through a cross section of the body, the cross section being oriented parallel to the yz plane and having an area equal to A, and where $\Delta T$ is the temperature drop along a distance $\Delta x$ measured along the x axis as can be measured by attaching to the body a pair of localized temperature sensors (thermometers), typically thermocouple junctions (thermocouples), that are spaced apart in the x direction by the distance $\Delta x$. A direct measurement technique that implements this one-dimensional heat flow is generally described in the textbook *Elementary Physics: Classical and Modern*, by Richard T. Weidner and Robert L. Sells, at pages 306–307 (1975).

In that technique, a sample body in the form of a solid circular cylinder ("rod"), having a uniform cross section a and having a pair of end surfaces, is surrounded by an insulating material, in order to minimize heat exchange into or out of the sample body through its side surfaces. One end surface of the body is maintained at a constant high temperature $T_h$, as by means of a hot reservoir or heat source, while the other end surface is maintained at a constant lower temperature $T_c$, as by means of a cold reservoir or heat sink. In the steady state, the heat crossing any cross section of the cylinder per unit time is equal to the same value P given by equation (1) above, and the temperature gradient $\Delta T/\Delta x$ is the same everywhere along the rod, i.e., is independent of the x coordinate.

In prior art, implementation of this sort of one-dimensional technique has been cumbersome and time-consuming, stemming from the need for attaching the heat reservoirs and the thermometers to the sample body each time a different one is to be measured. Also, relatively lengthy and careful measurements are required to account for, and correct for, heat losses. More specifically, the required thermal insulation tends to get in the way of the thermometers (thermocouple junctions) and their wiring, as well as in the way of the heat source and its wiring—the wiring, being fine (small diameter) and fragile, and having a tendency to develop kinks and to be crunched by the required thermal insulating material.

Relevant to solving these problems is U.S. Pat. No. 5,297,868 entitled "Measuring Thermal Conductivity and Apparatus Therefor" issued on Mar. 29, 1994. On the other hand, in some, if not many or most, cases it would be desirable to have available an even faster method for measuring thermal conductivity.

SUMMARY OF THE INVENTION

This invention is based on our discovery that in the case of a wide variety of electrically insulating crystalline or polycrystalline host materials that contain an impurity or a combination of impurities, and in particular the case of chemical vapor deposited (hereinafter: CVD) diamond as host material, the thermal resistivity, $W=1/\kappa$ by definition, satisfies the equation $$W = A + C\alpha \tag{2}$$

where $\alpha$ is the optical absorptivity of the individual bodies, and where C and A are constants, respectively, for all such bodies (polished or unpolished) formed by a given type of host material that contains a given type of impurity or a combination of given types of impurities in a given ratio in that material.

The optical absorptivity $\alpha$ ideally is defined by the equation $I = I_0 \exp(-\alpha t)$, but it is typically measured in practical cases according to the equation $$I = \beta I_0 \exp(-\alpha t) \tag{3}$$

where $\beta$ is a well known (correction) factor involving external surface reflections and multiple internal reflections (caused by the refractive index), where t is the thickness of the body parallel to the propagation direction of the optical radiation, where $I_0$ is the intensity of optical radiation of wavelength $\lambda$ incident on the body, and where I is the intensity of optical radiation of the same wavelength $\lambda$ emerging from the body. For example, in the case of CVD diamond, the factor $\beta$ is equal to 0.71, approximately.

As stated above, equation 2 is valid for all bodies of a host material having a combination of impurities in which the ratios of concentrations among the same impurities are all equal in all the bodies—for example, all bodies of naturally occurring, gem quality diamond containing the impurities boron and nitrogen in a ratio of 3/2 by weight, regardless of the total amount of the impurities (within reasonable limits) in each of the bodies.

In using the above equation (2), especially in practical cases, it is not necessary or desirable that the wavelength $\lambda$ be monochromatic or even nearly monochromatic. Instead $\lambda$ can encompass a wide range of the optical spectrum such as substantially the entire humanly visible range of the spectrum (approximately 400 nm–800 nm) or any range anywhere within the visible that preferably comprises wavelengths having significant intensities continuously spanning a range of spectral width approximately equal to at least 200 nm, so that ordinary sunshine or ordinary ambient artificial visible light can be used. As used here, the term "significant intensity" refers to an intensity that contributes to a measurement of the optical absorption $\alpha$ of a body. Alternatively, a convenient spectral range of wavelengths in the infrared region (e.g., approximate range of 800 nm–2,000 nm or 800 nm–10,000 nm) of the optical spectrum, preferably having wavelengths of significant intensities continuously spanning a range of spectral width equal to approximately at least 200 nm can be used, either alone or simultaneously advantageously combined with a convenient range in the visible range of the spectrum having wavelengths of significant intensities continuously spanning a range of spectral width approximately equal to at least 200 nm. Moreover, instead of—or preferably in addition to substantially the entire humanly visible range of the spectrum (approximately 400 nm–800 nm) or any range anywhere within the visible that preferably comprises wavelengths having significant intensities continuously spanning a range of spectral width approximately equal to at least 200 nm—a spectral range encompassing approximately 10 nm–10,000 nm can be used preferably having wavelengths of significant intensities continuously spanning a range of spectral width equal to approximately at least 200 nm.

Thus in cases where a given sample-body under test (hereinafter: "given sample" or "SUT") is known to have the same host material and the same type of impurity as two other bodies, the thermal resistivities $W_1=1/\kappa_1$ and $W_2 1/\kappa_2$ (with $W_1 \neq W_2$) the two other bodies can be measured using, for example, the apparatus and method described in the aforementioned U.S. Pat. No. 5,297,868, thereby yielding the constants A and C of equation 2 above by means of known mathematical techniques involving advantageously best curve-fitting of linear equations. Thus the value of the thermal resistivity $W_s$ of the given sample (SUT) can then be determined simply by measuring the optical absorptivity $\alpha$ of the SUT and determining the thermal resistivity W of the SUT from equation (2) above.

The thermal resistivities W for the first and second bodies and hence the thermal resistivity $W_s$ for the SUT can be thus measured in a direction either parallel or perpendicular to the plane of (i.e., either parallel or perpendicular to a major surface of), for example, a thin fill of CVD diamond by determining the optical absorptivities and the thermal resistivities of the first, second, and the SUT(s) in these directions, respectively.

As known in the mathematical art, if more accuracy is desired in determining the values of A and C, a selection of more than two other bodies can be used and measured for their respective values of $\alpha$ and W, and a best-fitting-straight-line technique can then be used to obtain best values of A and C.

In the case of CVD diamond, in which the main or predominant type of impurity tends to be some sort of carbon, the constants A and C tend to be independent of batches of diamonds made in a given CVD chamber under different conditions of such deposition parameters as temperature and pressure, and even independent of the growth technique including microwave plasma, hot filament, or arc jet in a given chamber, as well tend to be independent of the CVD chamber. It is believed that these independences are attributable to the fact that the impurity responsible for the optical absorptivity in all these bodies of CVD diamond is a similar form of some kind of carbon. However, it should be understood that this belief, or any theory for that matter, is not essential for the success of the invention.

In a specific embodiment, this invention involves apparatus for determining the thermal resistivity $W_s$ of an electrically insulating crystalline or polycrystalline sample (SUT) of host material, containing a concentration of an impurity or of a combination of impurities, the apparatus comprising a pair of first and second dividers. The first divider is connected to receive both an input $I_0$—advantageously in the spectral ranges specified above—representative of optical radiation directed on the SUT and an input I representative of the optical radiation emerging from the SUT. These inputs $I_0$ and I can be obtained by conventional methods or as are further described in our aforementioned patent application Graebner-Jin 12-111. An output $I_0 I$ emerging from the first divider thus is a representative of the ratio of the input-to-output intensity $I_0 I$ of the optical radiation directed on and emerging from the SUT. A natural logarithm converter is connected to receive this digital output of this first divider. This natural logarithm converter produces an output that is a representative of the natural logarithm ($\log_e$) of its digital input. The natural logarithm converter also is arranged to multiply its input $I_0 I$ by a factor $\beta=0.71$, approximately, for CVD diamonds as the host material—in order to take into account both external optical reflections and multiple internal reflections as mentioned above. Thus the output of the natural logarithm converter is a representative of $\log_e (\beta I_0/I)=\alpha_s t$, according to equation (3) above. The second divider is connected to receive the output of the natural logarithm converter and of a representative of the measurement of the thickness t of the SUT, whereby the output of this second divider is a representative of $\alpha_s$, the optical absorptivity of the SUT. A multiplier is connected to receive both this output $\alpha_s$ and a value of the constant C previously stored in a memory, this value of C having been previously determined experimentally using at least the first and second bodies, as described above. This multiplier then multiplies together the values of C and $\alpha_s$. An adder is connected to receive the resulting output $C\alpha_s$ of the multiplier as well as the value of the constant A previously stored in a memory, the value of A having been previously determined experimentally using at least the first and second bodies, as described above. The output of the adder is thus equal to $A+C\alpha_s$, which is equal to the thermal resistivity $W_s$ of the SUT, as follows from equation (2) above. A detector (or sensor or display device) is connected to receive this output $A+C\alpha_s$, which will thus be equal to the desired value of $W_s$. The detector can include amplifier circuitry for the purpose of calibration against known SUTs and for other circuitry purposes as known in the art. Analog to digital (hereinafter "A/D") converters can be strategically placed in the apparatus in the case circuit elements—i.e., the logarithm converter, the adder, the multiplier, and the dividers—are designed to process digital information rather than analog information, as known in the art.

Advantageously the optical absorptivity $\alpha_s$ of the sample (SUT) is measured in a spectral range having wavelengths of significant intensities continuously spanning a range of spectral width approximately equal to at least 200 nm, followed by determining the thermal resistivity $W_s$ of the sample (SUT) by determining the value of $A+C\alpha_s$, where A and C are the constants determined from the equation $W=A+C\alpha_s$, the values of C and A being determined by measuring the respective thermal resistivities $W_1$ and $W_2$ and by measuring the respective optical absorptivities $\alpha_1$ and $\alpha_2$ of at least first and second bodies comprising the same host material as that of the sample and the same impurity or combination of impurities as that of the sample, but the first and second bodies containing a different concentration of the impurity or of the combination of impurities from each other. It will be understood that $W_1$, $W_2$, $\alpha_1$ and $\alpha_2$ are determined by any suitable technique, e.g., the technique and apparatus of the above cited '868 patent.

Thus, having measured the optical absorptivities $\alpha$ and the thermal resistivities W of at least the first and second bodies, the thermal resistivity $W_1$ of the SUT (or that of each of a group of SUTs) can be determined by measuring only the optical absorptivity of the SUT (or the optical absorptivities $\alpha_s$ of each of the group of SUTs).

Although in the case of anisotropic host materials, the constants A and C can depend upon the direction of propagation of optical radiation and the direction of heat flow through the bodies, the constants A and C are independent of the concentration of the given type of impurities or the combination of the given types of impurities in the given ratio in that material. However, when making measurements of $\alpha$ and W, the same direction of propagation of optical radiation need not be used for measuring $\alpha$ as the direction of heat flow for measuring W; nevertheless, the direction of heat flow with respect to a major plane of the host materials advantageously is the same for the first and second bodies as for the SUTs.

Advantageously, in the cases in which the host material contains a combination of impurities, both in the first and second bodies these impurities have the same weight or molecular ratios among each other as in the SUT.

Advantageously also, the optical absorptivity $\alpha$ of each of the bodies, including the optical absorptivity $\alpha_s$ of the SUT, is measured by measuring the thickness of each of the bodies (such as by known techniques) and by directing a beam of optical radiation of the first (advantageously equal to the second) spectral range R on each of the bodies, followed by measuring the ratio of the optical intensity $I_0$ of the optical radiation directed on the respective body to the optical intensity I of the optical radiation emerging from the respective sample, in order to determine the optical absorptivity of the SUT via equation (3) above. Here the range R refers not only to the upper and lower limits of the spectral range but also to the spectral intensity distribution within the entire range R.

The constants A and C can also be determined by trial and error: that is to say, trial values of these constants A and C can be selected as a trial set: for a multiplicity of SUTs, trial values of $W_{st}=A+C\alpha_s$ can then be calculated using measured values of $\alpha_s$; these trial values of $W_{st}$ can then be compared with measured values of $W_s$ using some other technique of measuring $W_1$ for each of the SUTs, such as is taught in the aforementioned U.S. Pat. No. 5,297,868; and then a new trial set of constants A and C can be selected for a better set of trial values of A and C, and the process repeated until it converges.

BRIEF DESCRIPTION OF THE DRAWINGS

Elements that are the same, or are similar to one another, in different Figures are denoted by the same reference numerals or labels. Only for the sake of clarity, none of the Figures is drawn to any scale.

DETAILED DESCRIPTION

EXAMPLE 1: CVD DIAMONDS

Figure 1:
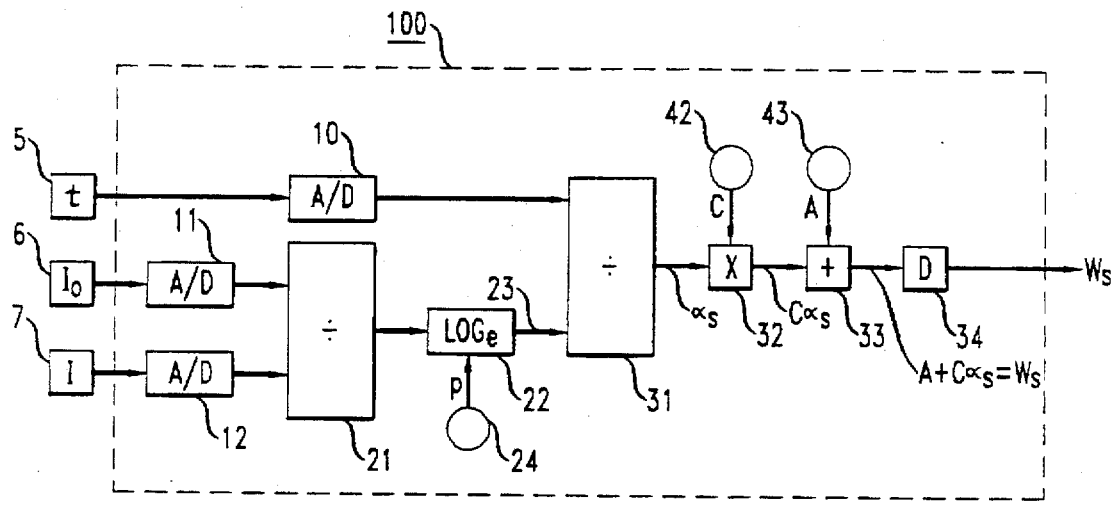
FIG. 1 is a diagram of apparatus in accordance with a specific embodiment of this invention.

At least two bodies of CVD diamond films are fabricated, each of the bodies having a major surface, and each of them having been made in the same or different CVD chambers under conditions that result in at least two of them having two different thermal conductivities $W_1$ and $W_2$, respectively, and hence having at least two different optical absorptivities $\alpha_1$ and $\alpha_2$, respectively. Their respective thermal conductivities W in the direction parallel to their major surfaces are respectively measured, for example, by the technique described in the aforementioned U.S. Pat. No. 5,297,868. Using sunlight or artificial source of visible light (the wavelengths $\lambda$ having significant intensities continuously spanning the approximate range of 400 nm–800 nm) as the source of optical radiation propagating through these bodies in the direction perpendicular to their major surfaces, their respective optical absorptivities $\alpha$ in this direction are respectively determined, for example, using equation (3) above.

Advantageously, the values of the optical absorptivities of the two (or more) bodies range over at least one, and preferably three, powers of ten. Then, in the case where W and $\alpha$ of two and only two bodies are used for these determinations of optical absorptivities, a straight line is drawn in a Cartesian graphical plot, either by hand or by machine, between the two resulting points of W vs. $\alpha$, whereby C and A can be determined: the slope of the straight line yields the value of C, and the intercept of the straight line with the ordinate (i.e., the point at which $\alpha=0$) in the Cartesian graphical plot yields the value of A. More specifically, if $W_1$ and $W_2$ denote the respective measured values of the thermal resistivities of the two bodies, and if $\alpha_1$ and $\alpha_2$ denote the respective measured values of the optical absorptivities of the two bodies, then it follows mathematically that $$C=(W_2-W_1)/(\alpha_2-\alpha_1), \text{ and } A=(\alpha_2 W_1-\alpha_1 W_2)/(\alpha_2-\alpha_1).$$

In the case where the values of W and $\alpha$ of more than two bodies are measured, well-known techniques of straight-line fitting—either human eye, human calculation (using, for example, least squares), or preferably computer machine—can be used to find a best-fitting straight line to fit the equation (2) above, whereby the values of C and A are determined from the slope and intercept of the best-fitting straight line.

Alternatively, having determined the value of the constant A as above, the value of the constant C can be determined as follows. The measured points (W–A)/A vs. $\alpha/\alpha_0$ are plotted on log-log paper, where $\alpha_0$ is a conveniently or arbitrarily selected constant, and where the base of the logarithm is immaterial—the points advantageously spanning at least one power of ten and preferably at least three powers of ten. That is to say, points corresponding to the logarithm of (W–A)/A (to any base of logarithms) are graphically plotted as ordinates (i.e., along a y axis) against the logarithm of $\alpha/\alpha_0$ (to the same base of the logarithms) as abscissae (i.e., along an x axis), the values of $\alpha/\alpha_0$ spanning at least one power of ten and preferably spanning at least three powers of ten. These points are fitted to a best-fitting straight line having a slope equal to unity, either by means of human eye or by means of well-known mathematical techniques (such as least squares) by human calculation or preferably by computer machine. The value of the constant C can then be determined from the ordinate of the intercept $y=y_0$ on the x axis of the resulting straight line log-log plot; i.e., the value of $y=y_0$ at which $x=0$—i.e., the value of y at which $\log(\alpha/\alpha_0)=0$—by means of the equation $$C=(A/\alpha_0)\text{antilog}(y_0) \tag{4}$$

as can be derived from equation (2) above.

As a source of optical radiation for measuring the optical absorptivities $\alpha$, instead of, or preferably in addition to a source of visible light, a source(s) of near infra-red optical radiation can be used. Advantageously, in any event the optical source should have wavelengths of significant intensities continuously spanning a range of spectral width approximately equal to at least 200 nm.

Having thus determined the values of C and A, an apparatus 100 of the kind shown in FIG. 1 can be used. As indicated in FIG. 1, the apparatus 100 includes a source of a signal representing the quantity t, the thickness; a source 6 of another signal representing the quantity $I_0$ of the SUT; and a source 7 of yet another signal representing the quantity I of the SUT. The apparatus 100 further includes three A/D converters, 10, 11, and 12, respectively, as well as two dividers 21 and 31, respectively. The A/D converter 10 is arranged to receive the input signal t representative of the thickness of the SUT. The A/D converter 11 is arranged to receive the input signal $I_0$ representative of optical radiation directed on the SUT, and the A/D converter 12 is arranged to receive the input signal I representative of the optical radiation emerging from the SUT. These inputs $I_0$ and I can be obtained by conventional methods such as described in, for example, *Optics Guide* 5, at pages 22–9 through 22–38 (1990), published by Melles Griot, Irvine, Calif. 92714, or as described below. Alternatively, the thickness inputs t and the intensity inputs I can be measured in a single apparatus as described in our aforementioned patent application Graebner-Jin 12-111.

The divider 21 is connected to receive the outputs of the A/D converters 11 and 12. An output signal emerging from the divider 21 thus is a (digital) representative of the ratio of the input-to-output intensity $I_0I$ of the optical radiation directed on and emerging from the SUT. The natural logarithm converter 22 is also arranged to receive an input β from a source 24—the same β as appears in equation (3) above, the value of β having been determined by known methods, and having been stored in the source 24—whereby the natural logarithm converter 22 multiplies its input $I_0I$ by this factor β, in order to take into account both external optical reflections and multiple internal reflections in the SUTs as discussed above in connection with equation (3). For the case of CVD diamond as the host material, the value of β is approximately equal to 0.71. Thus the output 23 of the natural logarithm converter 22 is thus a representative of $\log_e (\beta I_0/I) = \alpha_s t$, according to equation (3) above. The divider 31 is connected to receive the outputs of the A/D converter 10 and of the natural logarithm converter 22, whereby the output of this divider 31 is a representative of $\alpha_s$, the optical absorptivity of the SUT. A multiplier 32 is connected to receive both this output $\alpha_s$ and a value of the constant C previously stored in a memory 42—this value of C having been previously determined experimentally using at least the first and second bodies, as described above. This multiplier 32 then multiplies the values of C and $\alpha_s$. An adder 33 is connected to receive the resulting output $C\alpha_s$ of the multiplier 32 as well as the value of the constant A previously stored in a memory 43—the value of A having been previously determined experimentally using at least the first and second bodies, as described above. The output of the adder 33 is thus equal to $A+C\alpha_s$, which is equal to the thermal resistivity $W_s$ of the SUT, as follows from equation (2) above. A detector (or sensor or display device) 34 is connected to receive this output $A+C\alpha_s$, which will thus be equal to the desired value of $W_s$. detector 34 can include, in addition to a display device, amplifier circuitry for the purpose of calibration against known SUTs and for other circuitry purposes as known in the art.

Figure 2:
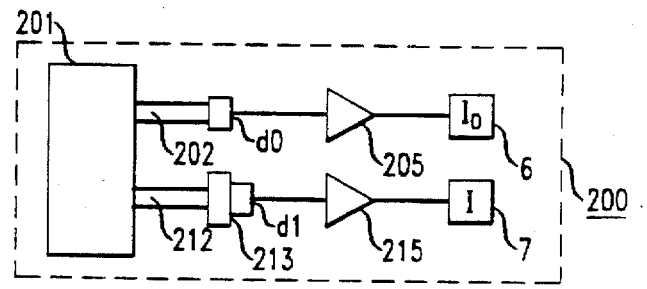
FIG. 2 is a diagram, partly in cross section, of apparatus useful for measuring the optical absorptivity of a host material, in accordance with another specific embodiment of the invention.

FIG. 2 shows apparatus 200 useful for simultaneously measuring the values of I and $I_0$, respectively, for the sources 6 and 7 (FIG. 1). Here in FIG. 2 a light source 201 is arranged in conjunction with a pair of optical fibers 202 and 212 to produce a pair of optical beams respectively incident on an optical detector d0 and on a sample 213. Another optical detector d1 is located behind the sample 213. These optical detectors d0 and d1 can be, for example, Group IV semiconductor optical detectors having PIN impurity structures or Group III–V semiconductor optical detectors as known in the art. Amplifiers 205 and 215 are arranged to receive the outputs of these detectors d0 and d1, respectively. The sources 6 and 7 are arranged to receive the output of the amplifiers 205 and 215, respectively. Calibration of the apparatus 200, to ensure that in the case of zero absorption by the sample 213 (or in the case of no sample 213 being present) the values of I and $I_0$ will be equal, can be achieved by adjusting the relative gains of the amplifiers 205 and 215, or by adjusting the relative intensities of the optical radiation propagating through the optical fibers 202 and 212, or by doing both of these adjustments.

Figure 3:
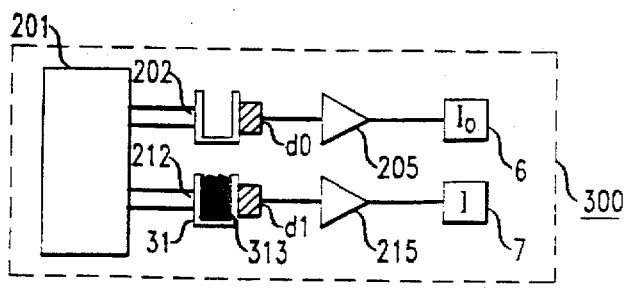
FIG. 3 is a diagram, partly in cross section, of another apparatus useful for measuring the optical absorptivity of a host material, in accordance with another specific embodiment of the invention.

FIG. 3 shows apparatus 300 also useful for simultaneously measuring the values of I and $I_0$, respectively, for the sources 6 and 7 (FIG. 1). Here in FIG. 2, however, the sample 313 is in powdered form and is held in place by a transparent container 31. For the purpose of symmetry, a similar transparent container 30 is placed behind the optical fiber 202. In all other respects, the apparatus 300 (FIG. 3) is the same as the apparatus 200 (FIG. 2).

Figure 4:
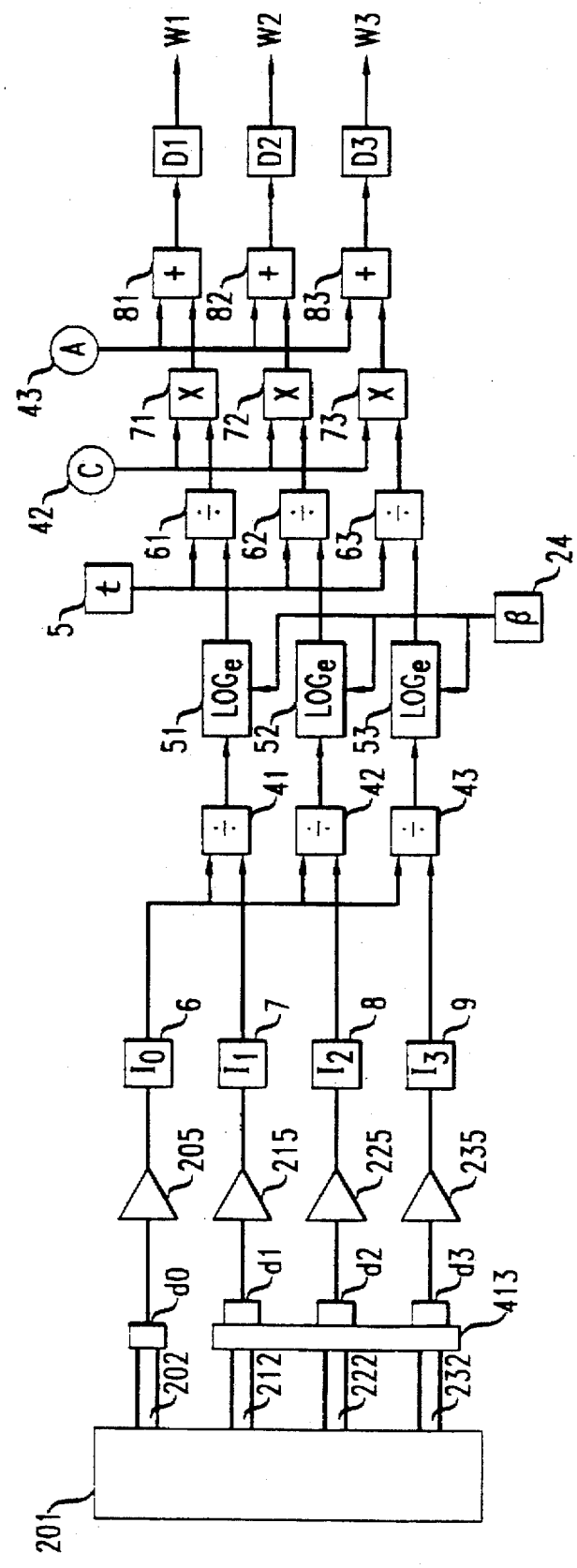
FIG. 4 is a diagram, partly in cross section, of yet another apparatus useful for measuring the optical absorptivity of a host material, in accordance with another specific embodiment of the invention.

FIG. 4 shows apparatus 400 useful for simultaneously determining the thermal resistivities W1, W2, W3 of three exemplary portions of a SUT 413—more than three portions being similarly simultaneously being determinable by simply adding in parallel more of the same type of elements that are shown in FIG. 4. As indicated in FIG. 4, four optical fibers 202, 212, 222, and 232 emanate from the optical source 201. The fiber 202 and an optical detector d0 are arranged so that the optical detector d0 receives the optical radiation propagating through this fiber 202. The fibers 212, 222, and 232 are arranged so that a major surface of each of the three exemplary portions of the SUT 413 receives the optical radiation propagating through these fibers 212, 222, and 232, respectively. Optical detectors d1, d2, and d3—each similar to the detectors d0 and d1 described above—are arranged on an opposing major surface of the SUT 413 so as to receive the optical radiation emanating from the three exemplary portions of the SUT 413, respectively, whereby the detectors d0, d1, d2, and d3 produce four respective outputs representative of the optical radiation emanating respectively from no SUT and the three exemplary portions of the SUT 413. Amplifiers 205, 215, 225, and 235 are arranged to receive these four outputs, respectively, and to produce four respective amplifier outputs that are delivered to four respective sources 6, 7, 8, and 9 of signals $I_0$, $I_1$, $I_2$, and $I_3$ representative of the intensities of the optical radiation sensed by the detector d0, d1, d2, and d3, respectively.

As further indicated in FIG. 4, dividers 41, 42, and 43 are arranged to receive both the signal $I_0$ from the source 6 and a respective one of the signals $I_1$, $I_2$, and $I_3$ from the sources 7, 8, and 9, respectively, whereby the dividers 41, 42, and 43 produce respective divider outputs representative of $I_1/I_0$, $I_2/I_0$, and $I_3/I_0$, respectively. Each of natural logarithm converters 51, 52, and 53 is arranged to receive the input β from the source 24 and to receive a respective one of these divider outputs, whereby the outputs of the logarithm converters 51, 52, and 53 are representatives of $\log_e (\beta I_0/I_1) = \alpha_1 t$, $\log_e (\beta I_0/I_2) = \alpha_2 t$, and $\log_e (\beta I_0/I_3) = \alpha_3 t$, respectively, where $\alpha_1$, $\alpha_2$, and $\alpha_3$ are the respective as (=optical absorptivities) of the three portions of the SUT 413, all according to equation (3) above—assuming that the thickness of these three portions of the SUT 413 are substantially equal.

Each of three further dividers 61, 62, and 63 is arranged to receive an input from a source 5 representative of the thickness t of the SUT 413—again assuming that the thickness of these three portions of the SUT 413 are substantially equal—as well as a respective one of the outputs of the logarithm converters 51, 52, and 53. These dividers 61, 62, and 63 thus produce outputs that are representative of $\alpha_1$, $\alpha_2$, and $\alpha_3$, respectively—i.e., the optical absorptivities of the three portions of the SUT 413.

Each of three multipliers 71, 72, and 73 is arranged to receive an input from the source 42 in which the value of the constant, C as defined in equation (2) above, has been previously determined experimentally and stored, as described above. In addition, each of these three multipliers 71, 72, and 73 is arranged to receive a respective one of the inputs $\alpha_1$, $\alpha_2$, and $\alpha_3$ from the dividers 61, 62, and 63, respectively. These multipliers 71, 72, and 73 thus produce respective outputs representative of $C\alpha_1$, $C\alpha_2$, and $C\alpha_3$.

Each of three adders 81, 82, and 83 is arranged to receive an input from the source 42 in which the value of the constant, A as defined in equation (2) above, has been previously determined experimentally and stored, as described above. In addition, each of these three multipliers 71, 72, and 73 is arranged to receive a respective one of the inputs $\alpha_1$, $\alpha_2$, and $\alpha_3$ from the dividers 61, 62, and 63, respectively. These multipliers 71, 72, and 73 thus produce respective outputs representative of $A+C\alpha_1$, $A+C\alpha_2$, and $A+C\alpha_3$—that is to say, outputs that are representative of the thermal resistivities $W_1$, $W_2$, and $W_3$ of the three portions of the SUT 413.

Each of three detectors D1, D2, and D3 is arranged to receive a respective one of the outputs of the adders 81, 82, and 83. Each of these detectors D1, D2, and D3 can include sensing and amplifier circuitry, for calibrating each of the outputs $W_1$, $W_2$, and $W_3$ with respect to known SUTs 413, as well as a display device.

It was assumed above that the thickness t of the SUT 413 does not significantly vary across the SUT and hence that the three portions of the SUT 413 had the same thickness t. If, however, the thickness does vary significantly from one portion of the sample 413 to another, then instead of a single source 5 of a single signal representative of the thickness t, there are three sources of three different signals $t_1$, $t_2$, and $t_3$ representative of the three thicknesses of the sample 413 at locations at which the optical detectors $d_1$, $d_2$, and $d_3$ are located. In such a case, each of the three dividers 61, 62, and 63 is arranged to receive a respective one of the three different signals $t_1$, $t_2$, and $t_3$ instead of the same signal representative of t.

An advantageous alternative to purely visible light, the optical radiation contains significant wavelengths spanning the approximate spectral range anywhere between 10–10,000 nm, the source preferably having wavelengths of significant intensities spanning continuously a range of spectral width approximately equal to at least 200 nm. Still another advantageous alternative source of optical radiation is a source of infra-red radiation (which preferably is combined with visible light) spanning the approximate spectral range of anywhere between 800 nm–10,000 nm, preferably having wavelengths of significant intensities spanning continuously a range of spectral width approximately equal to at least 200 nm.

Instead of measuring the optical absorpitives $\alpha$ and thermal resistivities W of the CVD diamond films and of measuring the optical absorptivity the SUT in the direction parallel to the major surface of the respective films, these quantities can be measured, and especially W should be measured, in a direction perpendicular to the major surface of the bodies, whereby the thermal resistivity of the SUT in this direction can be determined.

EXAMPLE 2: NATURAL DIAMONDS

Provided that the natural diamonds are sufficiently pure, equation (2) above still holds with the same C and A for all those diamonds having the same single impurity or having impurities in the same proportion among one another. More specifically, in the cases of naturally occurring diamonds: for a given impurity—such as boron (blue diamond) or nitrogen (yellow diamond)—the values of A and C in a given crystalline direction are all the same from diamond body-to diamond-body provided, for example, that they all contain one and the same type of impurity or a combination of the same types of impurities in a fixed ratio—such as boron, or such as nitrogen, or such as boron and nitrogen in a weight ratio of E/F, where E and F are constants. Typically, diamonds found in the same vein of a diamond mine will satisfy this impurity requirement. More specifically, it is expected that all naturally occurring diamonds originating from the same vein of a mine will contain the same type of impurity but in different impurity concentrations in different locations of the vein. For a body of pure diamond (i.e., containing no significant concentration of any impurities that cause optical absorption), its thermal resistivity W will be equal to $W_0 = A + C\alpha_0$, where $W_0$ is the thermal resistivity of the body of pure diamond, and where $\alpha_0$ is the optical absorptivity of the body of pure diamond. Thus, by measuring and determining the C and A for diamonds from a given vein where at different locations of the vein the optical absorptivity is different, the thermal resistivity W can be determined for all other diamonds in this vein simply by measuring their respective optical absorptivity followed by using equation (2) above.

Although the invention has been described in detail in terms of specific embodiments, various modification can be made without departing from the scope of the invention. For example, instead of diamond other crystalline or polycrystalline host materials can be used such as lithium niobate or lithium fluoride containing various impurities, sapphire (typically containing titanium as the impurity), or ruby (typically containing chromium as the impurity). Moreover, one of the A/D converters 11 or 12 can be omitted provided the divider 21 is arranged to receive the quantities I and $I_0$ simultaneously or seriatim—in the latter case of which either the remaining A/D converter 11 or 12 or the divider 21 is provided with a temporary memory for storing one of the quantities representative of I or $I_0$. Also, instead of the apparatus for measuring $\alpha$ depicted above in FIGS. 2–4, the apparatus taught in the aforementioned patent application Graebner-Jin 12-111 can be used. The A/D converters 10, 11, and 12 can be omitted provided the other circuit elements—i.e., the logarithm converter 22, the multiplier 32, the adder 33, and the dividers 21 and 31—can process analog information, as known in the art. One of the A/D converters 11 or 12 can be omitted provided the divider 21 is arranged to receive the quantities I and $I_0$ simultaneously or seriatim—in the latter case of which either the remaining A/D converter 11 or 12 or the divider 21 is provided with a temporary memory for storing one of the quantities representative of I or $I_0$. Moreover, the A/D converters 10, 11, and 12 can be omitted provided the other circuit elements—i.e., the logarithm converter 22, the multiplier 32, the adder 33, and the dividers 21 and 31—can process analog information, as known in the art. Finally, the logarithm converter 22 need not be a converter to natural logarithms (i. e., to the base e of natural logarithms) but can be a converter to logarithms to other bases, such as to the base ten or to any arbitrary base x, provided suitable changes in the mathematics are made—such as dividing the output of the logarithm converter by a factor $\log_e 10$ or $\log_x e$, respectively, in order to obtain the values of the thickness t, or by redefining the value of the constant C in equation (2) above by dividing it by a factor $\log_e 10$ or by a factor of $\log_e 10$: that is to say, for example, that the value of C stored in the memory 42 should be divided by this factor $\log_e 10$ or $\log_e 10$, respectively.

What is claimed is:

1. Apparatus for determining the thermal resistivity W s of an electrically insulating crystalline polycrystalline sample of host material, the host material containing a concentration of an impurity or of a combination of impurities, comprising (a) a first divider connected to receive both an input signal $I_0$ representative of optical radiation directed on the sample and an input signal I representative of the optical radiation emerging from the sample, whereby the first divider can produce a first divider output that is representative of the ratio of $I_0/I$;

(b) a logarithm converter connected to receive the first output and to multiply the first input by a factor β, whereby the logarithm converter can produce a logarithm converter output that is representative of the thickness t of the sample multiplied by the optical absorptivity $\alpha_s$, of the sample;

(c) a second divider connected to receive the logarithm converter output and to receive an input signal representative of the thickness t of the sample, whereby the second divider can produce a second output that is a representative of the optical absorptivity $\alpha_s$ of the sample;

(d) a multiplier connected to receive both this second output and a constant output C from a first memory that stores the constant C, this value of C having been previously determined experimentally using at least a first body and a second body having the same host materials as that of the sample and the same impurity or combination of impurities as that of the sample for determining the value of the constant C, whereby the multiplier can produce a multiplier output that is a representative of $C\alpha_s$; and (e) an adder connected to receive the multiplier output and a constant output A from a second memory that stores the constant A, this value of A having been previously determined experimentally using said at least first and second bodies, the adder producing an adder output that is representative of $A+C\alpha_s$, the adder output being representative of the thermal resistivity $W_s$ of the sample, where the experimentally determined constants A and C are determined by measuring the thermal resistivities $W_1$, and $W_2$ and the optical absorptivities $\alpha_1$ and $\alpha_2$ of said at least first and second bodies, respectively, using any well known or prior art apparatus and technique.

2. The apparatus of claim 1 in which the host material is CVD diamond.

3. The apparatus of claim 1 in which the host material is natural diamond.

4. The apparatus of claim 1 in which the host material is ruby.

5. The apparatus of claim 1 in which the host material is sapphire.

6. The apparatus of claim 1 in which the host material is lithium niobate.

7. The apparatus of claim 1 in which the host material is lithium fluoride.

8. The apparatus of claim 1 further comprising a display device connected to receive the adder output.

9. Apparatus according to claim 1 further comprising:

a first and a second source of a first and a second optical beam, respectively;

a first optical detector arranged to receive the first optical beam, whereby the first optical detector produces the signal $I_0$;

a first major surface of the sample of host material being arranged to receive the second optical beam, the second detector being arranged to receive the resulting optical radiation emerging from a second major surface of the sample, whereby the second optical detector produces the signal I.

10. The apparatus of claim 9 in which the host material is CVD diamond.

11. The apparatus of claim 9 further comprising a container in which the sample is located, the sample of host material being in powdered form.

12. The apparatus of claim 11 in which the host material is CVD diamond.

* * * * *